United States Patent [19]
Ledden et al.

[11] Patent Number: 6,093,546
[45] Date of Patent: Jul. 25, 2000

[54] PROCESS FOR PREPARING TEST ELEMENTS

[75] Inventors: David J. Ledden; David R. Moorman; Michael J. Kinch, all of Indianapolis, Ind.; Harvey B. Buck, Weilheim, Germany

[73] Assignee: Roche Diagnostics, Indianapolis, Ind.

[21] Appl. No.: 07/940,062

[22] Filed: Sep. 3, 1992

[51] Int. Cl.⁷ .................. G01N 33/53; G01N 33/543; G01N 33/544; G01N 33/551

[52] U.S. Cl. ............... 435/7.1; 435/7.92; 436/518; 436/524; 436/527; 436/528; 436/529; 436/530; 436/534

[58] Field of Search ................... 436/518, 524, 436/527, 528, 529, 530, 534; 435/7.1, 7.92

[56] References Cited

U.S. PATENT DOCUMENTS

| | | | |
|---|---|---|---|
| 4,128,629 | 12/1978 | Eldred et al. | 424/1 |
| 4,478,946 | 10/1984 | Van der Merwe et al. | 436/518 |
| 4,591,571 | 5/1986 | Kuboyama et al. | 436/533 |
| 4,812,414 | 3/1989 | Warren, III et al. | 436/533 |
| 4,828,980 | 5/1989 | Synder et al. | 437/7 |
| 4,916,056 | 4/1990 | Brown et al. | 435/7.92 |
| 4,933,435 | 6/1990 | Ngo | 530/413 |
| 5,075,220 | 12/1991 | Pronovost | 435/7.36 |
| 5,177,005 | 1/1993 | Lloyd et al. | 435/94 |

*Primary Examiner*—Rebecca E. Prouty
*Attorney, Agent, or Firm*—Fulbright & Jaworski, LLP

[57] ABSTRACT

The invention relates to a process for making a test element, such as an analytical test element. Compositions of matter, such as analyte specific receptors, are treated to carry a charge. These are then applied to test carriers treated to carry a charge opposite that of the composition of matter. Interaction of charge fixes the composition of matter to the test element.

28 Claims, 8 Drawing Sheets

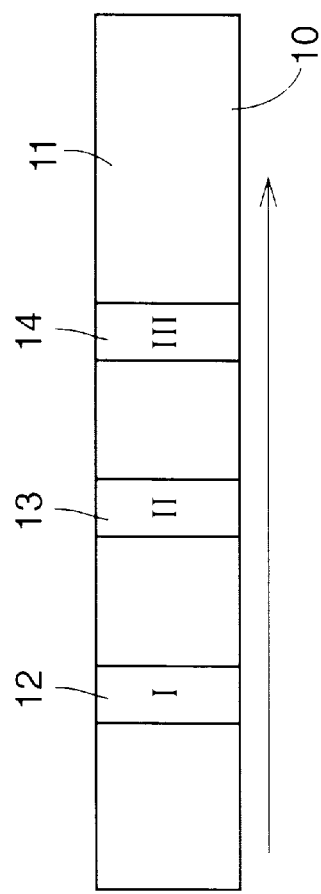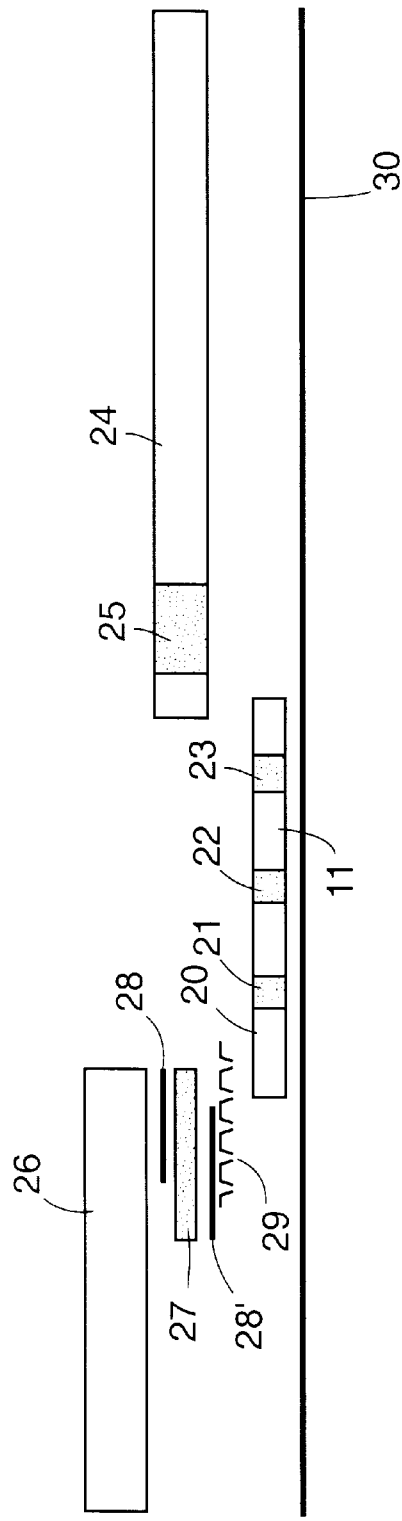

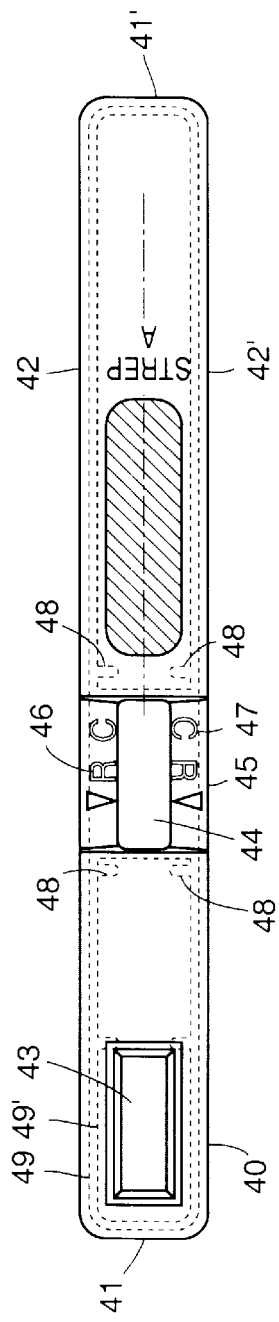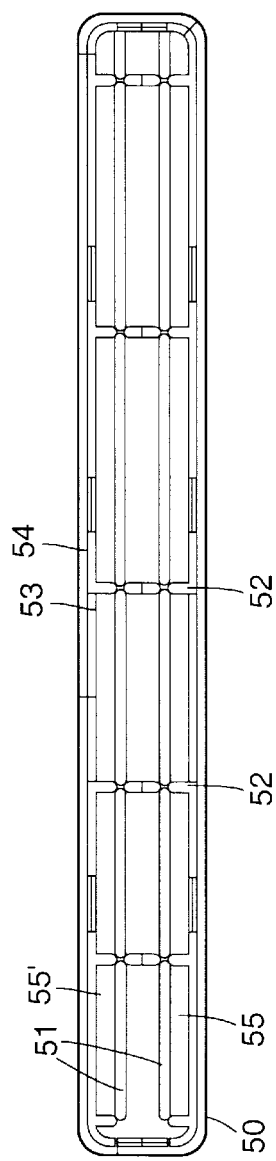

PROCESS FOR PREPARING TEST ELEMENTS

FIELD OF THE INVENTION

This invention relates to the field of clinical diagnosis. More particularly, it relates to dry chemistry based analytical devices, processes for manufacturing these, as well as their use.

BACKGROUND AND PRIOR ART

Clinical diagnosis relates, in general, to the determination and measurement of various substances which relate to the health or general status of an individual. Physicians, health care workers, and the general public as well are concerned about the presence and levels of various substances in body fluids such as blood, urine, and so forth. Among the substances which have been measured in clinical analysis for a long time are glucose, cholesterol, and various enzymes such as amylase and creatine kinase. More recently, determinations as to pregnancy, blood disorders ("Quick's" tests, Partial thromboblastin time or "Ptt" tests, etc.), and infections have also become routine in clinical diagnosis. Of most pressing concern to the field, e.g., is the determination of antibodies to human immunodeficiency virus (HIV), as a marker for Acquired Immune Deficiency Syndrome ("AIDS") or Aids Related Complex ("ARC"). The new tests for this virus, however, build on a broad and deep base of earlier advances in the field.

An oversimplification which nonetheless serves to place the subject invention in proper context is division of the field into "wet chemistry" and "dry chemistry". The former pertains to methodologies where a reaction takes place completely in a liquid state. Exemplary of such chemistries is U.S. Pat. No. 4,818,692, which describes an alpha amylase assay. Review of this reference shows that a reagent is added to a liquid sample, and, if the analyte of interest (amylase) is present, the reagent reacts with it, yielding a color. The development and intensity of the color are monitored as a determination of the presence and amount of the analyte ("Analyte" as used hereafter, in any context, refers to a substance to be determined). "Dry chemistry", in contrast, involves the placement of some or all of the reagents which are involved in determination of an analyte under consideration onto a solid material, such as a paper strip. The sample is brought into contact with the solid material, and some or all of the reactions which are necessary for the detection of the analyte in question take place in situ. If additional reactions involving reagents not found on the solid material are required, these can be added after the preliminary reactions take place. The invention concerns dry chemistry, and therefore wet chemistry is not discussed hereafter.

The art is filled with many different examples of dry chemistry apparatus used for clinical analysis. Examples of some of the patents in the field include U.S. Pat. Nos. 4,446,232, to Liotta, 4,361,537 to Deutsch et al., and 4,861,711 to Friesen et al.

Liotta teaches a very simple example of a zoned test strip useful in immunodiagnostics. A support such as a paper strip has enzyme linked antibodies positioned in the strip, as well as a reagent which can react with the enzyme label. When analyte for which the antibody is specific is contacted to the strip, the antibodies bind with the analyte and diffuse to the point in the strip where the substrate reagent is found. There, enzyme-substrate interactions take place resulting in a color forming reaction, indicating the presence of analyte in the sample.

If analyte is not present, then the conjugate is immobilized in the "solid phase" zone, preventing interaction of enzyme and substrate.

The Deutsch patent teaches a test strip which is contained in what is essentially a capped test tube. The test strip has various reagents positioned along its length. When liquid is introduced at one end of the strip, it moves via capillarity up the strip, and various reactions take place along it.

Friesen et al. teaches several zoned devices in which different forms of immunological reactions, such as competitive and sandwich immunoassays can take place.

These three patents show the general efficacy of test strips based upon fibrous materials, such as paper, in various forms of diagnostics. Many other patents show similar teachings, including U.S. Pat. Nos. 3,888,629 (Bagshawe), 4,366,241 (Tom et al.) 4,517,288 (Giegel et al.), 4,668,619 (Greenquist et al.), 4,708,932 (Axen et al.), 4,774,174 (Giegel et al.) 4,786,606 (Giegel et al.), 4,824,640 (Hildebrand et al.), and 4,855,240 (Rosenstein et al.). All of these patents show the general applicability of solid test strips for clinical analysis. Tom et al., for example, at columns 19–26, which are incorporated by reference herein, gives a roster of some of the various analytes which may be assayed by using dry chemistry. Dry chemistry is also taught in connection with the analysis of specific analytes, such as cholesterol (U.S. Pat. No. 3,983,005, to Goodhue et al.), human chorionic gonadotropin (U.S. Pat. No. 4,496,654 to Katz et al.), hemoglobin (U.S. Pat. No. 4,742,002, to Guadagno), and blood type antigens (U.S. Pat. No. 4,851,210, to Hewett).

While analytical test strips of the type described supra are popular, they are not without their problems. Strips made of bibulous materials such as paper, e.g., are subject to wide fluctuations in the quality and properties of the materials used. In addition, impregnation or placement of reagents, such as antibodies on the strip may require processes which lead to degradation of the reagent. For example, if a protein reagent is applied to a test strip in a liquid form, it must of course be dried. Drying may require heat, however, and heat is one of the most notorious inactivators of proteins. Further, due to the inherent absorptive nature of bibulous materials such as paper, it is difficult, if not impossible, to control the eventual distribution of the reagents on the strips when one is attempting to incorporate reagents in a predefined, prescribed, or preferred fashion. Even when extremely stringent criteria of quality control are used, since the capillarity of paper, e.g., can vary not only from strip to strip but even within a single strip, preparation of a strip always carries a risk. Additionally, fibrous materials are not inert. When assaying for an analyte, it usually happens that a certain amount of it will adhere to the fibers of the strip rather than to reactants, such as antibodies placed on the strip. As a result, interpreting a particular test strip can be very difficult.

Given the concerns set out supra, as well as others which are not repeated here but are well known to the art, there have been attempts to use other materials. Different fibrous and gel or film materials have been used as supports, but these are not altogether satisfactory for many of the reasons set forth herein. Attention has therefore turned to other materials, including particulate matter such as beads or spheres made of "inert" materials. "Inert" as used herein simply means that the material does not interfere with reactions which are involved in the clinical application under consideration. To say that there are many patents relating to the use of inert particles in clinical and immunological assays is to understate the case. A sampling of some of the U.S. Patents in this area include U.S. Pat. Nos.

4,794,090 (Parham et al.), 4,740,468 (Weng et al.), 4,680,274 (Sakai et al.), 4,657,739 (Yasuda et al.), 4,478,946 (VanderMerwe et al.), 4,438,239 (Rembaum et al.), 4,340,564 (Harte et al.), 4,338,094 (Elahi), 4,201,763 (Monthony et al.), 4,166,102 (Johnson) and 4,059,658 (Johnson). The vast majority of the literature relating to the use of "active" or "loaded" particles, however, is not at all pertinent to this invention. In general, particulate material is used in wet chemistry systems, such as agglutination assays, along the lines of those described supra. A solution containing particles having receptors, such as antibodies bound thereto, is added to a sample being analyzed. If the analyte in question is present in the sample, it binds to the receptor which is itself bound to the particle. As a result of the binding, the particles agglutinate for any of a number of different reasons. Such applications of particle technology are not pertinent to this invention.

Microparticles present both advantages and disadvantages when used in preparation of analytical devices. The advantages include their uniform size. Also, they increase surface area on which reactions can take place without a need for increased sample volumes. As a result, the speed of reaction can increase. Disadvantages include the possibility of undesirable uncontrolled aggregation of the beads. Also, non specific binding can result in false reactions. When particles are placed in fibrous matrices, they can move, thus confusing results via a "blurring" effect.

Somewhat more pertinent to this invention are apparatus where particulate material carrying, e.g., a receptor, is contained in a carrier, such as a test strip. The patents to Weng et al. and Yasuda et al. are exemplary of such systems. The problem with the use of particles, such as beads in porous carriers, however, is that the particles, left to themselves, can move in the fibrous matrix, not unlike a ball or marble rolling on a carpet. This tendency to move is exacerbated when a flowing material, such as a liquid, is added to the matrix. The particles then move throughout the device and even off of it with the moving solution front, rendering the test strip useless.

A different approach to the field of clinical diagnosis attempts to avoid these problems by not using fibrous matrices at all or using fiber in a separate layer. Such an approach is exemplified by, e.g., U.S. Pat. No. 4,258,001, to Pierce. This patent teaches a dual layer system, where one layer is a structure made of particles bound together by an adhesive. The patent describes the particles as possibly containing a so-called "interactive composition" such as an antigen or antibody. This layer is positioned on a support. Analyte containing liquid passes through the porous particle layer, and the analyte reacts with the interactive composition.

A system along the lines of that described by Pierce, however, is not without its problems. Adhesives, by their nature, are sticky. Even when dried, a certain amount of "tack" is present which, although small, may not be insignificant with respect to sample analyte. As a result, false binding to adhesive, rather than to the "interactive composition" may occur. In addition, there is some difficulty in the manufacture of uniform arrays of adhered beads, because distribution of the beads may not be uniform, and the drying of adhesive may occur at different rates, depending on parameters, such as thickness of the array.

Recently, the art has seen some approaches to this problem. U.S. Pat. No. 4,916,056, to Brown, III et al., suggests that by selecting an appropriate fibrous matrix and particles of a particular size, one can immobilize the latter in the former. At column 8, lines 60–65 the inventors concede that the reason for this is not known, and review of the disclosure in its entirety gives no information as to any treatment applied to the particles. European Patent Application Number 200 381 also teaches the use of beads with antibodies bound to them in a matrix; however, this disclosure states, that while the beads are trapped within the matrix, they are nonetheless mobile. Such a test strip is not completely satisfactory for use in clinical assays.

One of the consequences of advances in fields related to clinical chemistry, such as immunology, is that many applications of the field which were once deemed sophisticated have now become quite commonplace. One result of this development has been the creation of a home diagnostic market, i.e., a subfield of clinical chemistry in which an individual performs an assay at home, rather than having a health professional perform it. The home user is not trained in the interpretation of clinical parameters, and as such home diagnostic products are generally restricted either to systems where a "yes/no" type of test is used, or one where an unambiguous answer is provided by the test apparatus used. The patent literature shows examples of devices useful in home diagnostics in Brown III et al., U.S. Pat. No. 4,916,056, discussed above, and in Valkirs et al., U.S. Pat. No. 4,632,901. Both disclosures are drawn in particular to self diagnosis of pregnancy, and point to the need in such systems for an adequate negative control. Indeed, the art has long recognized the desirability and necessity for "onboard" controls in test strips. Examples of disclosures teaching these are U.S. Pat. Nos. 4,649,121 (Ismail et al.), 4,558,013 (Markinovich et al.), 4,541,987 (Guadagno), 4,540,659 (Litman et al.), 4,472,353 (Moore), and 4,099,886 (Olveira). The use of controls on many of these devices shows that they are useful for the skilled practitioner as well as for the home user. The art shows that both "negative" and "positive" controls are used. A "negative" test is one which will inform the user that the test sample does not contain the analyte of interest. In contrast, a true negative "control", as the phrase is used herein, should never give a signal if reagents are operating properly. This is true regardless of whether or not the analyte of interest is present.

A positive control essentially tells the user that the system and device are functional. Such controls may contain samples of the analyte of interest and the reagent components which are essential to the reaction which must take place to identify analyte in a test sample. Positive controls should always generate a signal when an analytical device containing one is used. If a signal is not generated, then the user has an indication that the apparatus is no longer functional. Thus, positive controls can serve to "date" a test strip by checking the system or reagent integrity. They can also indicate when a test strip or other system component has been stored improperly, or where quality control has not been adequate. Given continued growth in the diagnostic market, positive controls loom as being more and more important.

As has been indicated supra, among the stresses to which analytical apparatuses are subjected are long periods of storage. Others include improper use or negligent handling. Such stresses may jeopardize the integrity of the apparatus, and may also damage it. It will be clear, of course, that test strips and other analytical apparatus should not be exposed to the environment prior to their intended use in analysis of a sample. Exposure to the environment, e.g., may result in physical harm and/or chemical contamination of the strip. Thus it is clear that these apparatus are desirably protected until used.

The desirability of protecting the strip must be balanced by the cost of providing it. Given the enormous volume of test strips used by clinical laboratories, physicians offices and so forth, the cost must be kept as low as possible. To that end, many of these devices are packaged cheaply with, e.g., cellophane or plastic, in the form of bags, pouches, etc. Such packaging provides a certain amount of protection, but serve no useful purpose in connection with the use of the strip. Since many of the test strips in the art are used in analysis of infectious materials, and in connection with biological samples such as blood, urine, sputum, feces, and so forth, it is desirable that the protection afforded the test strip also serve to minimize contact of the individual using the strip with the sample. Additionally, since it is desirable for these strips to be configured so that they can be used without any sophisticated knowledge on the part of the user, ideally the casing for the strip should make it easy for the user to employ the device. Also, the protection or casing structure ideally should be configured to act as a "fail-safe" system, if, e.g., too much sample is added to the device. Other desirable features of such a casing include viewing ports or "windows" as well as fluid reservoirs, both of which are described infra.

While the art does show the use of test strip holders and casings which move in the direction of the above cited goals, none of these achieve all of them. Examples of casings or holders for test strips are seen in, e.g., U.S. Pat. Nos. 4,900,663 (Wie et al.), 4,851,210 (Hewett) and 4,331,650 (Brewer et al.), which show the less sturdy type of holder described supra. Frequently these devices are referred to as "test cards", given the nature of their configuration. More substantial holders may be seen in GB 2204398 EP 306 772, EP 323605, EP 306336 and EP 183442. None of these devices possess all of the desired properties, e.g., protection, low cost, and ease of use.

To summarize the art, there are approaches to test strip design which utilize bibulous paper and/or particle technologies. Each of these has advantages and/or problems. The prior art teaches the use of controls, both "positive" and "negative" for use in diagnostic assays. Different types of configurations are available, but a test strip which incorporates a positive control, a negative control, and a testing area is not seen in the art.

Test strips and devices of the type described herein are frequently enclosed in a casing or housing. These structures permit the actual strip to be used in a manner that ensures optimal results. Such casing or housings should be "inert", i.e., they should not contain any material which will interfere with the assay or test which is carried out on the test strip.

Important aspects of test strip housing include protection of the user from the fluid or sample being tested. Further, the casing must protect the actual strip from premature contact with other fluids. Such "premature" contact can include contact with a fluid that is not being analyzed, as well as the contact of a zone or region within the strip prior to the desired time of contact. Thus, where a set of sequential reactions or reaction steps must take place, the casing or housing can play an important role in regulating these steps.

In addition, the type of structure described herein, via appropriate placement of viewing means such as "ports", "windows" or other openings can facilitate the analysis of a test fluid. Also, the housing, if constructed in an appropriate manner, will prevent interference with the natural chromatographic nature of the test strip by inappropriate contact with other surfaces.

Other features of a housing or casing which must be considered include inertness to the assay. The housing should be made of material which does not interfere with the assay, reagents, or sample. The housing should also be configured in a way that makes it easy to observe the test, without causing problems such as the casting of shadows or otherwise impeding proper viewing of the reaction. In addition, since the amount of sample applied to the test strip will vary from user to user, it is desirable that the holder be configured to prevent overflow or flooding of different sections of the test strip in those situations where excess fluid is added.

Thus, it is the purpose of this invention to provide a useful analytical apparatus which can be used in determining an analyte in a sample, where the apparatus contains a negative control, a testing area, and a positive control, preferably, but not necessarily, in a linear array of zones placed within a continuous matrix.

It is also a purpose of the invention to provide a process and methodology useful in manufacturing such apparatus, which combines the benefits of both matrix and particle technologies. The discovery of a way in which molecules such as proteins, glycoproteins, and other substances can be attached to surfaces such as beads and then to fibers without chemical coupling solves many of the problems associated with combining particle and fiber technologies.

It is a further object of the invention to provide a casing or holder for a test strip which protects the test strip itself, simplifies its use by the investigator, and also, surprisingly, helps serves as a fail-safe system to facilitate the take up of sample fluid by the test strip in a controlled manner.

How these, as well as other aspects of the invention are achieved will be seen from the disclosure which follows.

SUMMARY OF THE INVENTION

This invention is based upon several surprising discoveries, beginning with the observation that molecules such as, but not limited to proteins, can be secured to both a solid carrier and a fiber without the use of an adhesive connecting the particles to each other. In fact, this is to be avoided. The molecule of interest is attached to the carrier, preferably via a covalent bond, and is then treated with a solution at a pH different from the isoelectric point (pI) of the molecule attached to the carrier. This treatment imparts a charge to the carrier attached molecule. The matrix, such as a glass fiber matrix, either possesses an inherent charge (in the case of glass fibers, this is negative), or can be treated to acquire one. By choosing the treatments and matrices so that the carrier bound molecule and matrix have opposing charges, the complex can be positioned in the matrix, in contrast to devices where an adhered array of particles is positioned on it.

The invention encompasses, inter alia analytical apparatus with on board positive and negative controls. It has been found that the force of attraction between the solid carrier bound molecule and the matrix is so strong that exquisitely accurate placement of the carrier/molecule complex on the matrix is possible, without diffusion throughout the porous matrix. Essentially, the carrier stays exactly where it is placed, and as a result, the analytical reaction takes place at one and only one position. Due to this desirable result, one can place both positive and negative controls within the same apparatus, as there need not be any concern as to the mixing of reagents within the strip once sample is added thereto.

The placement of the carriers throughout the strip means that the control and test reactions will always take place at a particular position on the device. Therefore, one can provide a carrier which is arrayed so that the top presents a viewing means which specifically indicates where test and control reactions should take place. In addition, because the reagent placement is so well defined, one can be less rigorous about the amount of sample applied to the apparatus. This can be a concern because if the absorptive capacity of the test strip is exceeded, problems with reagent mingling and washout might result. Thus, the test carrier provided to hold the strip is configured to provide a reservoir for the imbibing of test liquid as the strip can do so.

These main features, as well as additional inventive features not described in this Summary, will be explained in greater detail in the text which follows.

BRIEF DESCRIPTION OF THE FIGURES

FIG. 1 displays a broad embodiment of the test apparatus described herein.

FIG. 2 shows the test apparatus with additional optional features.

FIG. 3a is a top view of the top of an embodiment of the casing for the apparatus.

FIG. 3b shows a top view of the bottom of a casing for the apparatus.

DETAILED DESCRIPTION OF PREFERRED EMBODIMENTS

Figure 4:
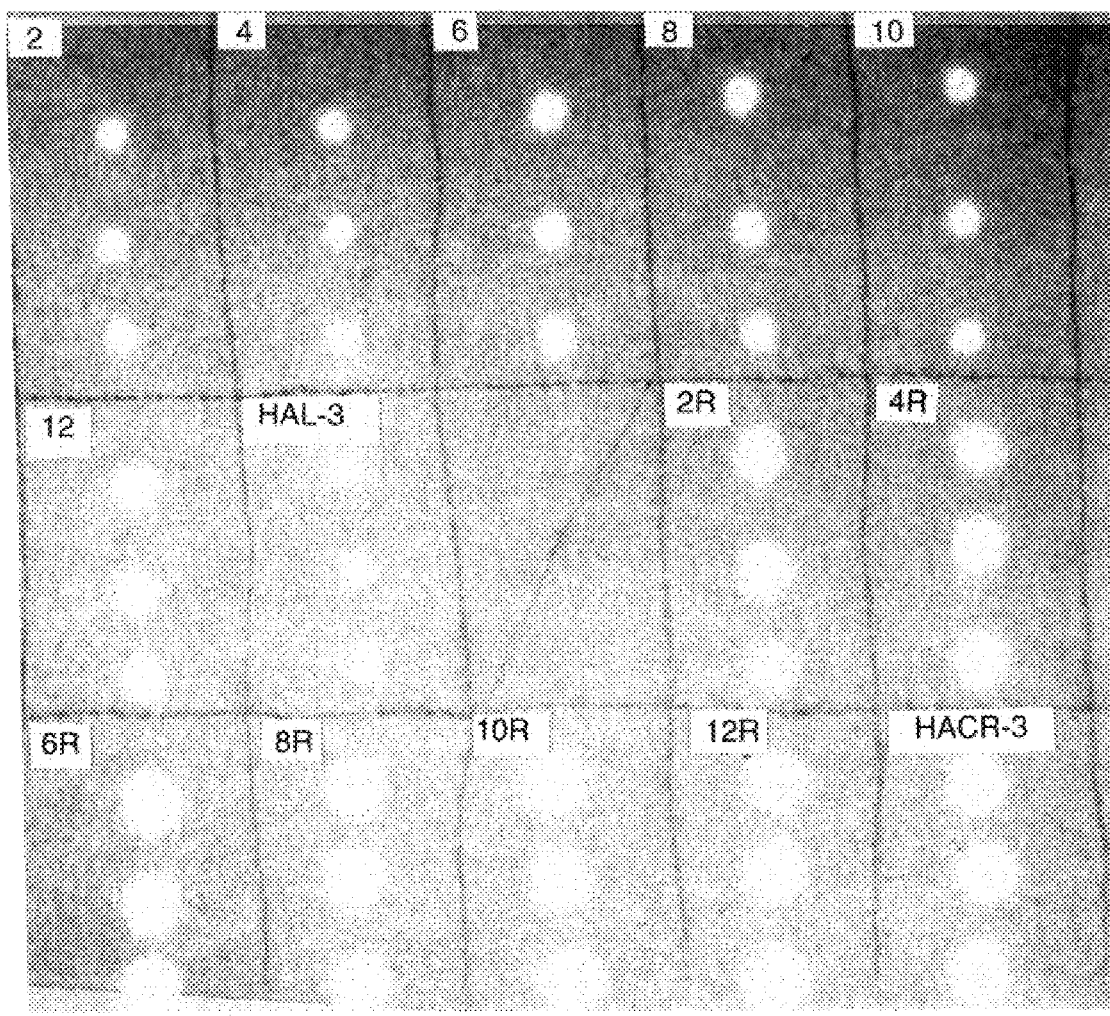
FIG. 4 presents the results of interaction of glass microfiber paper with charged latex, shown using fluorescence.

Referring now to the figures, FIG. 1 shows schematically the analytical apparatus of the invention in its broadest embodiment. A test strip 10 comprises an absorptive matrix 11, composed of material such as bibulous paper, cellulose, or other material capable of imbibing a liquid sample. The horizontal arrow shows the direction of flow of fluid in the apparatus.

Now, referring to the items depicted at "12", "13" and "14" these show a negative control, "read" or "test" region, and positive control, respectively, positioned in a linear array. Each of these regions I, II and III contains reagents described infra.

The negative control "I" is designed as a marker for the integrity of the test system. This region or zone should never present a signal, such as a color change. For example, if the matrix 11 is white, bibulous paper, region 12 should be white both before and after the test analysis is carried out. If it is not, then there is something wrong with the apparatus and it should either be destroyed if there is a color present prior to the assay or the test results must be discarded if a color appears after the test is run. Ideally, this region contains a reagent similar to those used in the other zones, but one which is non reactive or inert relative to the analyte being examined. For example, if the analyte of interest is an antigen, such as a Streptococcus A antigen which will be detected via an antibody-antigen reaction at "II", the negative control may contain inactivated or non-immune immunoglobulin or antibodies of the same species present in region II. Similarly, if the test in question is one for HIV antibodies where the test region contains viral antigens, then region I should contain inactive forms of the antigen, such as heat or urea treated material, so that the epitopes to which the antibodies bind are disrupted. Additional materials which can be considered for use in the negative control include inactivated forms of protein A, biotin-streptavidin/avidin complexes, and so forth. Non-immune IgG has been mentioned, and this is exemplary of non-immunoactive forms of antibodies and immunoglobulin in general.

Referring to FIG. 1, and reference "13" or "II", this constitutes the test region and is where the actual analytical assay takes place. This region contains a reagent which will react with the analyte of interest. For example, using the two analytes mentioned supra, if Streptococcus pyrogenes is being assayed, this region may contain antibodies, polyclonal or monoclonal, which specifically bind to Strep A group specific antigen. Antibodies to Strep A are known from the literature, and need not be elaborated upon here. It is to be understood, of course, that "antibodies" refers not only to the complete molecule, but also reactive fragments such as Fab, Fab', Fv and F(ab')$_2$ fragments and the like.

Ideally, but not essentially, the reagent is bound to a solid carrier, as described infra, and is placed in the strip such that it is immobile. This placement is also true if one is assaying for, e.g., HIV antibodies, and in this case the reagent in "II" is, for example, an epitopically active viral protein or fragment of the virus. Many such proteins and fragments are known and need not be recited here. In a device useful in assaying for HIV or other materials which have many recognized epitopic molecules, a plurality of test zones may be positioned in between the positive and negative control. HIV, for example, can be assayed for by positioning test zones containing receptors specific for gp120, p24, gp41, antibodies to these molecules etc. In a similar fashion, the device may be constructed for "TORCH" testing by positioning of test zones containing receptors which will bind antibodies specific for Toxoplasma, Rubella, Herpes and Cytomegalovirus.

The analyte and reagent in II react if the analyte is present in the sample, preferably immobilizing the analyte at zone II. The fluid sample, due to the capillarity of the strip, flow to the third zone III or "14", which is the positive control zone. This zone will contain a sample of the analyte of interest as well as a sample of reagent identical to that deployed in the second zone. As a result, this zone should always evidence a reaction. If it does not, then the test is not valid. Thus, the third zone also serves as a functional control for the assay reagents and the strip structure itself.

In an especially preferred embodiment, once the reactions between sample and the reagents in zones II and III take place, an additional reagent is brought into contact with these zones, so as to result in the formation of a detectable signal, such as a color. For example, when strep A is being assayed, following immobilization of the group specific antigen by an antibody at the second zone, a second, labelled antibody is contacted to this zone, as well as to the third, positive zone. Since some strep group antigen molecules are multiepitopic, a sandwich of antibody-antigen-labeled antibody can, and does form. The label may inherently possess a signal, such as a radionucleid or chemiluminescent moiety, colored or fluorescent particles, gold and dye sols or can be one which engages in a further reaction or reactions to generate a signal. Most preferably, these labels are enzymes such as but not limited to peroxidase, alkaline phosphatase or β-galactosidase. When these labels are used, it is necessary that additional materials, such as enzyme substrates be added to the strips. Examples, of these include tetramethylbenzidine (TMB), 4-chloro and 4-methoxy-1-naphthol for peroxidase catalyzed reactions and 5-bromo-4-chloro-3-indolyl phosphate (BCIP) or BCIP and a tetrazolium salt for alkaline phosphatase catalyzed reactions. These 2 examples are by no means exhaustive of the available substrates, and the choice of substrate will depend on what is available plus the particular enzyme used. Preferred substrates are those upon which the actions of enzymes yield a product which is insoluble in aqueous media.

Both the second labeled antibody and the substrate may be applied to the apparatus from an external source, or can be positioned within the device itself. A second, supporting layer, e.g., underneath the test zones, can permit percolation up into the device, or the device can be configured such that substrate is contained in a layer connected to structure 10 via a flap means, where this layer can only contact the test regions upon application of external force, such as pressure.

A particularly preferred embodiment of the invention has the substrate deployed in situ in an optional structure. This is shown in FIG. 2 and is discussed infra.

The three zones, i.e., negative (21), test (22) and positive zones (23), are positioned in a linear array relative to each other and separated from each other by at least a small amount of space, so that separate and discreet signals may be generated and determined.

If nothing has gone amiss in the manufacture, storage and use of the apparatus, there are only two possible results. If no analyte of interest is present, zone 21 will give no signal nor will zone 22. In contrast, zone 23 must give one, and the user will note only a single band on the device. In contrast, if analyte is present, both of zones 22 and 23 will give a positive signal, while zone 21 will not. Therefore, in evaluating the sample, it is a simple question of how many bands appear on the surface of the strip. Two bands indicate analyte presence, whereas one band indicates none. As has been explained supra, other considerations as to the validity of the test result are determined from band formation as well.

In apparatus where a multitude of various analytes are to be situated and assayed, such as "TORCH" assays described supra or assays for different or multiple epitope recognition, such as in HIV determination, a plurality of bands corresponding to a plurality of test zones will be present, each of which corresponds to a test for a different analyte.

In FIG. 2 a waste zone 24 is added to the end of the strip for absorption of the fluid after it has traversed zones 21, 22 and 23. The waste zone is preferably constructed of absorptive material which is at least as absorptive as the material out of which matrix 11 is made. On one level this feature may be seen as a convenience rather than a necessity, as other approaches to removing the fluid, such as by contact with an absorbent sponge, may be envisioned. It can be rendered explicitly functional by incorporating therein an agent which allows the user to determine whether the strip has been exposed to moisture or extremes of acid or base. The art is familiar with substances such as anhydrous copper sulfate, which changes from white to brilliant blue in the presence of liquid, as well as pH indicators which either change color or form a color when exposed to acidic or basic conditions. By incorporating these into the waste zone, one can ascertain if the strip has been exposed to undesirable conditions prior to use. In addition, such indicators can also serve as visual monitors that the strip device is functioning properly with respect to chromatographic flow. While such indicators may be placed anywhere in the device, placement along the waste zone ensures that there is no potential interference with the test reactions.

In addition, this zone can include so called "signal inhibitors" which prevent reaction of label and reaction partner to generate a signal. Such inhibition is desirable because if such a signal is generated here, "backflow" can carry the signal into the device to a point where it would interfere with the actual reaction signal.

Such indicators may conveniently be placed in the waste zone at the position identified as 25 in FIG. 2. This can also be the site for incorporation of an inhibitor for the signal generating system. In such cases an additional "port" or "window" is simply incorporated in the case enclosure to allow for visualization of indicator reactions. Examples of such inhibitors include sodium azide, which inhibits, irreversibly, the action of peroxidase. By incorporating the inhibitor in the waste zone, no significant generation of color or other signal in the waste or reservoir takes place as the result of interactions between signal generating system components. In turn, this helps to preserve test result stability since there is no backwash of color onto the matrix after the assay has been run.

Very desirable features are present in the depicted device at the end opposite the waste zone. Structure 26 comprises absorptive material for application of a liquid thereto. Its role will become clear in connection with components 27–29 shown in FIG. 2, discussed as follows. Item 27 is a structure, such as a pad, which contains a substance or substances, such as the substrates referred to supra. It is separated from structure 26 over its forward portion by a piece of double stick tape 28. A second piece of double stick tape 28' separates the substrate pad 27 from flow regulating means 29, which is in turn in one-way fluid contact with the test strip 11.

In operation, structures 26–29 come into play, e.g., when a sample has already been added to the strip and this has been followed by application of a labelled receptor. Exemplary of this situation is one where a strep antigen has been bound to antibodies on a bead, followed by the binding to the antigen of a second sample of antibodies, containing an enzyme label. In order to determine the binding, nonbound labelled receptor must be washed away and substrate must reach this zone. In order to prevent the need for a separate supply of the substrate reagent, in the embodiment of FIG. 2 an amount of the substrate is contained, in removable form, in structure 27, the "substrate pad". The substrate cannot be removed until it is moistened, and to that end adsorptive means 26 is positioned above the substrate pad. The moistening agent, or "run buffer" in, a preferred embodiment, is applied to 26 at some point along its length and it moves down and into the substrate pad. In this way material 26 serves as a "metering" device for delivery of fluid to structure 27. In order to guarantee that the liquid goes only into the front end of the substrate pad, double stick tape "28" is provided. This blocks the liquid from going forward, forcing it to move down and into the substrate pad. Additional types of blocking materials may be employed for this purpose, such as hardened hot melt adhesives. In practice, double stick tape is preferred.

The liquid or run buffer enters the substrate pad and dissolves/mobilizes the substrate contained therein. Again, to direct the flow of liquid forward, a second block or piece of double stick tape 28' is provided. This prevents the liquid from flowing backward. As can be seen in FIG. 2, this second block is positioned at the end of the substrate zone opposite the end where the first block is positioned. In the fashion described, means 28 and 28' are used in combination to establish a predefined channel for directional fluid flow through component 27.

The placement of tape 28' directs the flow of solubilized substrate into the extremely useful structure "29", referred to herein as a flow regulator or flow directing means. Structure 29 is a piece of non-wettable material which only permits flow of liquid downward, because of the configuration of its pores. As will be seen, the structure is characterized by conical or inverted "V" shaped pores. These permit downward flow, but do not permit flow up or across the structure. This flow director 29 is in fluid contact with the matrix 11, so the solubilized/mobilized substrate moves unilaterally into the matrix.

In addition to the aforementioned functions, structure 29 may be selected from materials with multiple pore sizes and thus used to control the "rate" of fluid flow from component 27 into component 11. Due to uniform placement of pores in structure 29 a uniform dispersion of fluid entering structure 11 is insured. Structure 29 may also be employed as a reagent delivery device by the application and drying of said reagents into the pores of structure 29. Methods of application and drying of reagents will be obvious to those skilled in the art and do not need to be elaborated upon here.

The choice of what materials constitute the structures "26" and "27" is limited only by the requirement that they be absorbent and inert relative to the reagents which contact them. Similarly, structures "28" and "28'", described as double stick tape, may be made of any materials which prevent the flow of liquid. The material chosen for structure 29 should be one which directs liquid in a single direction. A particularly preferred material for structure 29 is "Vispore", a material used in the manufacture of disposable diapers and described in U.S. Pat. Nos. 3,929,135 and 4,342,314, the disclosures of which are incorporated by reference herein. The '135 patent describes the structure of the material as a "tapered capillary", and indeed, one may view the conical or inverted V configuration as such. Hereinafter, "flow director having a tapered capillary pore structure" will refer to the type of material shown in the '135 patent.

The entire apparatus described herein is placed on an inert support 30. This serves merely to give added strength to the apparatus, and may be transparent if reading from the bottom of the strip element is desired, or not. The method of attachment of the strip components to the inert support may involve the use of double stick tape, hardened hot melt adhesives, a combination of the two, and/or other materials with suitable adhesive properties, all of which are known to the art.

Additional features may be incorporated into the apparatus. Non-limiting examples of these include analyte specific antibodies, signal inhibitors, buffers, and so forth.

The apparatus provides a one piece, horizontal flow test device which can be used for all purposes of a particular analysis test. One can apply sample, and additional active reactants and interpret test results all within the same device.

A very important feature of the preferred embodiments of the invention is the use of a "true" positive control. As discussed supra, in a preferred embodiment of the device both a sample of the analyte of interest and an active reactant, such as an antibody specific for the analyte, can be incorporated such that they will react if the analyte sample is solubilized. Such a control is desirable because it gives assurance that active reactant positioned at a different point in the device and designed to react with sample analyte remains active.

Other advantages of the device will be apparent by reviewing this disclosure as a whole.

A particular preferred embodiment of the test strips described herein involves the use of a process by which the receptor material is placed in the matrix. It has been found that the receptor or matrix incorporated molecule of interest can be applied thereto without the use of an adhesive or fixative by applying a charge to the matrix incorporated molecule. The molecule then carries a charge, and interacts with a charge carried by the matrix itself. By selecting materials as the matrix which have a charge opposite that of the molecules of interest, or by applying a charge to the matrix opposite that of the charge carried by the molecule, the latter is incorporated securely into the matrix, without the use of an adhesive or fixative. A particular advantage of the use of the charge interaction to place the receptor material in the matrix is the ability to control the impregnation or positioning of the receptor therein.

The material of interest, referred to hereafter as a composition of matter, may be in the form of the molecules themselves, or, in a preferred embodiment, attached to a solid carrier.

In order to apply charge to the composition of matter, various methods, including the positioning of the material in a charged field can be used. It is particularly preferred, however, to apply the charge by treating the composition of matter in a solution which has a pH that differs from the isoelectric point ("pI") of the material, i.e., the receptor, of interest. When a pH which differs from the pI is used, the composition of matter accepts a charge therefrom. At a pH below the pI, the composition of matter picks up a positive charge, whereas at a pH above the pI, the received charge is negative.

While pI values are generally associated with proteins, they are possessed by all molecules including carbohydrates, lipids, and the various combinations thereof (glycoproteins, lipoproteins, glycolipids, etc.). Thus, when a term such as "protein containing" or "carbohydrate containing" is used hereafter to describe a molecule, it refers to pure species of the molecule as well as the combination molecules. A glycoprotein antigen, for example, is both a "carbohydrate containing molecule" and a "protein containing molecule".

Particular types of molecules of interest and encompassed by this invention include all of the standard immunological reagents such as antibodies, be they polyclonal or monoclonal and their fragments and complexes, antigens, including fragments of antigens which are epitopically active, protein A, protein G, biotin, avidin, streptavidin, and so forth.

When the composition of matter consists of a receptor and a solid material, the former is bound to the latter. Among the materials which can be used for the solid carrier are synthetic, natural, and "semi-synthetic" materials, which refers to materials which can incorporate both naturally occurring and synthetic material in the carrier. Latex, polystyrene latex, glass, sepharose, dextran, agarose, silica, mica, clay, diatoms, and other materials can be used, with latex based polymers being particularly preferred.

The shape of the carrier is not critical, and it can include, e.g., rod, rhomboidal, and spherical shaped materials, the last of these being especially preferred. While not critical, it is desirable that the carrier particles be of uniform size, such as latex beads having an average diameter of from about 20 nm to about 20 um. Preferred beads have an average diameter of from about 0.3 um to about 1.0 um, and a particularly preferred embodiment employs beads having an average diameter in the range of from about 0.4 um to about 0.5 um.

To monitor the placement of the carrier material on the matrix during any manufacturing processes, it is desirable to use a carrier which is fluorescent or colored, although this is not essential.

As indicated supra, it is preferred to treat the compositions of matter with a solution having a pH which differs from the pI of the receptor. Generally, the solution may have a pH of from about 2.0 to about 12.0, a pH of from about 3.0 to about 9.0 being specially preferred. The choice of pH for the treating solution will vary, based upon the nature of the molecule, its pI, and other factors.

The matrix material, as indicated supra may possess an inherent charge, or it may be treated to possess one. Glass fiber, for example, inherently possesses a negative charge, so if a matrix containing glass fibers is used the composition of matter should be treated so that it carries a positive charge (e.g., treating solution at a pH below the pI), and the matrix does not have to be treated itself. Other matrix materials which do not possess a charge may be treated to receive one. Matrices can be treated with, e.g., acids or bases to protonate or deprotonate existing functional groups or by partial hydrolysis to generate new functional groups. Other modifications such as periodate oxidation of aldehydic functions to carboxyl groups, succinylation of amino functional groups by anhydride treatment or placement of matrices in electric fields may be employed. Non-limiting examples of materials which may be used as matrices include fibrous or bibulous materials, such as filter paper, regenerated cellulose or rag based papers, combinations containing cellulose, cotton, or glass fibers, as well as other fibrous materials. Polyamide and polyacrylamide are examples of fibrous or bibulous synthetics. The various fleeces used in analytical testing may also be used, as can films, gelatins, and so forth, all of which are to be included within the scope of this invention. Non-fibrous or non-woven membrane materials may also be employed. Examples of materials which may be used include nylon, nitrocellulose, cellulose acetate, and PVDF.

In preparing test matrices, the composition of matter is applied to the matrix, and any solution in which the composition is contained is then removed. This results in an incorporation of the composition in the test matrix. Due to the strength of the interaction of the opposing charges, the composition is bound where it was placed. Additionally, because like charges repel each other, the problem of clumping associated with solid carriers such as beads is eliminated. Using this invention, the solid carrier material is dispersed throughout the matrix, but only where it is disposed. This makes the manufacture of zoned devices, such as the three zone devices described supra extremely simple and permits accurate and sensitive evaluation of an analyte being assayed.

Test strips made in accordance with the dispersion of the composition of matter described supra can be subjected to further treatment as well, so as to result in analytical devices useful in various types of assays. For example, following the incorporation of a first receptor into the apparatus so that it is immovably incorporated therein, a second receptor which is mobile in the presence of a fluid can be added. If this second receptor is labeled, the resulting apparatus is useful in a sandwich type of immunoassay. When a sample containing the analyte of interest is added to the apparatus, a sandwich of bound receptor, analyte and previously mobile, labeled receptor results, after which the label can be determined. Of course, the second receptor, such as an antibody, can be added from a different source, i.e., it need not be incorporated in the device.

The skilled artisan will of course note that test strips prepared in accordance with this invention can also be adopted for use in competitive and displacement type of assays, with modifications to the test strip in accordance with standard protocols for preparation of test strips for these categories of assays.

It is also possible to prepare test strips in accordance with the process described herein for carrying out multianalyte, or concentration type of assays. By "multianalyte" systems, it is meant that the strip is adapted to identify more than one analyte. This is useful, e.g., when the need arises to determine what group(s) of Streptococcus is involved in a patient's infection or a patients response to a series of HIV antigens such as p24, gp41 and gp120. In the same manner the strip apparatus may be configured to perform "TORCH" testing when zone 2 of element 11 has been constructed with the antigens necessary to detect specific antibodies to Toxoplasma, Rubella, Herpes Simplex and Cytomegalovirus to determine what infection a patient may have. As a "concentration assay" is meant a system where one is to determine whether an analyte of interest is present in excess of insufficiency in a sample. In diagnosing diabetes, for example, the amount of glucose present in a body fluid sample is the key parameter that is measured. A test strip can be set up having a plurality of zones, as shown in FIG. 1, but where the color reactions in zones will represent a semi-quantitative measure of the analyte "concentration" in the sample. For example, if the first zone contains an amount of receptor just sufficient to react with all of the glucose found in a body fluid sample from a normal individual, the following zones can be used as a monitor for excess or toxic levels, because signals should not register in the following zones unless there is an abnormally large amount of analyte present. Similarly, in situations where, e.g., a hormone deficiency is suspected, one can calibrate the device so that the first and second zones contain just enough reagent to react with a normal amount of hormone. Using this approach, if no signal, or a weak signal is generated at the second zone, this is indicative of an abnormally low amount of the analyte.

Test apparatus of the type described herein are advantageously kept in a casing. Such a casing can not only provide protection to the test strip and safety to the user, but can also facilitate the use of the device in carrying out test analysis, as will be shown from the discussion that follows.

Referring to FIG. 3a this shows a top view of a casing 40, used in connection with the test device. The top of the casing is an elongated structure made of an inert and tough material such as polystyrene plastic. A rectangular structure with opposing short sides 41 and 41' and opposing longer sides 42 and 42' is provided. Referring to 40, from left to right, the top of the casing contains an application port 43, which is discussed at greater length infra. This port slopes downward from the opening, and provides a point for application of run buffer to the test strip so as to release any reagents contained therein, as explained supra. Moving toward the opposite end of the device a second port 44 is provided, which also slopes downward. This port is positioned over the three zones of the strip device, i.e., the negative control (21), read (22), and positive control (23) described supra. In practice, the sample to be analyzed, as well as possible other reagents, are added here. Again, the port slopes downward. The angle at which the walls of the port slope is selected so as to minimize shadowing, which can adversely affect interpretation of results. In the embodiment shown, the arrow 45, "R" 46, and "C" 47 are presented to aid in the use of the device. The arrow indicates where the sample to be analyzed is to be added, and "R" and "C" stand for the "read" or test and "control" or positive zones, respectively. Toward the end of the apparatus the shaded portion is an optional design embodiment.

A plurality of tabsets or joining means 48 protrude from dorsal side of the top of the casing, and are positioned to engage corresponding tabsets (52) in the bottom portion of the casing. Dotted lines 49 and 49' show that the underside of this portion of the casing is recessed to create what is in effect a slightly smaller rectangle within a larger one. The bottom portion of the device, in FIG. 3b described infra depicts the inner and outer walls of that portion of the structure more clearly, and a parallel configuration is present in the top portion, which engages the bottom portion.

Referring now to FIG. 3b, this is an open top view of the bottom portion 50 of the casing. This is made of the same material as the top portion, and has the same geometrical configuration. A pair of longitudinal bars 51 is present on the bottom of the casing and, together with a plurality of pairs of tabsets 52 define a guide for positioning of the test strip therein and also serve to hold the strip off the bottom of the housing. At least some of these tabsets combine with parallel tabsets in the top portion of the casing to form a joined structure when the top and bottom of the casings fit together. The bottom has, around its perimeter an inside wall 53 and an outside wall 54, which align with equivalent structures 49 and 49' in the top of the casing 40.

An important feature of the housing top is that it is configured so that the four walls of port 44 do not quite touch the test strip positioned therein. The result is that a small capillary space is created which in turn allows port 44 to retain sample and other reagents, and effectively "meters" application thereof to the test strip. Also, because the casing material does not directly contact the test strip, there are no uncontrolled or unrecognized effects on the properties of the test strip itself.

A similar type of structure results from the interpolation of tabsets protruding from the top and bottom of the casing. When these tabsets interact with each other, they effectively seal the enclosed strip element, resulting in formation of at least two reservoirs which retain excess fluid. To elaborate, it will be seen in FIG. 3b that hollow spaces 55 and 55' extend over the length of the housing along the length of the test strip. These spaces can hold liquid and, if too much is added at either of ports 43 or 44, this can result in overflow of the strip device. The sealing of casing parts 40 and 50 creates discrete overlfow compartments by interaction of the tabsets, however, resulting in retention of the excess fluid (such as sample and reagents) in the compartment immediately adjacent to the application point until the test strip is ready to absorb it. In effect, this interaction results in another metering means, insuring that liquid applied to the strip device enters the strip only at the desired location.

The top and bottom portions are fitted together and sealed after the actual test device or apparatus is positioned in the bottom portion thereof. The manner of sealing is up to the artisan. Examples of various ways the sealing can be accomplished are adhesives, application of heat, snap fitting or via sonic energy. It is also conceivable, though not likely, that the casing will be constructed so that the top and bottom portions can be detached and the test strip removed.

The actual operation of the invention as described herein will now be shown via the examples which follow.

EXAMPLE 1

Particles conjugated with an antibody were prepared in accordance with the invention. To do this, fluorescent carboxylated latex having a nominal mean particle diameter of 0.51 microns, were prepared as a 2.5% (w/v) solids suspension, using 0.02% (w/v) sodium azide/0.02% thimersol.

Anti-strep A rabbit polyclonal antibody was coupled to these particles via carbodiimide linkages. The final product was a 0.5% (w/v) solids suspension, stored in 100 mM glycine/50 mM HEPES/150 mM sodium chloride/0.1% (w/v) bovine serum albumin/0.1% (w/v) sodium azide, and 0.01% (w/v) thimerosal. The entire composition was at a pH of 7.4.

Samples were then prepared for testing by diluting aliquots of the latex to 0.26% solids (w/v), using 50 mM sodium phosphate/150 mM sodium chloride, at pH 7.2, followed by transfer to 15 ml centrifuge tubes (Corex), together with buffers of various type and pH, as discussed below. Samples were centrifuged at 9900 rpm (11,700×g max) for 15 minutes, and supernatants were aspirated and discarded.

Latex particles were resuspended at 0.27% (w/v) of solids in test buffer. Each suspension was sonicated prior to dilution to 0.005% (w/v) for determination of particle size distribution. The results are summarized in Table 1:

| Test Buffer | Antibody | Particle Diameter (nm) | CV (%) |
| --- | --- | --- | --- |
| 50 mM sodium phosphate (pH 2) | + | 472 | 13.5 |
| 50 mM sodium phosphate (pH 3) | + | 445 | 24.5 |
| 50 mM sodium phosphate (pH 4) | + | 641 | 50.5 |
| 50 mM phosphate/saline (pH 7.2) | + | 491 | 20.6 |
| 50 mM acetic acid (pH 3) | + | 477 | 15.7 |
| 50 mM phosphate/saline (pH 7.2) | − | 371 | 17.0 |

Antibody on particles caused aggregation at a pH of 4, whereas the pH values above and below this yielded particles with very similar distribution means, and which were only slightly greater than underivatized latex (note the coefficient of variation or "CV").

The CV values show that at pH values of 2, 3 and 7.2, particles were essentially monodisperse.

The various species which make up the polyclonal antibody preparation have isoelectric points ("pIs") which vary from 5 to 8. Since the antibody is being coupled to carboxylated latex the isoelectric point of the latex-antibody conjugate would be somewhat lower than a weighted average of the isoelectric points of the coupled antibody species. Surface charge repulsion is an important factor in maintaining the latex-antibody conjugate in a nonaggregated state and it is likely that at pH 4 a significant proportion of the antibody-latex particles would have insufficient net surface charge to prevent such aggregation.

EXAMPLE 2

The interaction of charged complexes of antibody and latex with a solid support was studied.

The process of Example 1 was followed to attach antibodies to latex particles. Additional samples were prepared by diluting aliquots of underivatized latex to 0.5% (w/v) solids with the same dilution buffer described in Example 1. Separate aliquots of the underivatized latex and antibody-latex conjugates were transferred to 2 ml microcentrifuge tubes together with the various buffers of Table 1. Samples were centrifuged at 14,000 rpm (16,000×g max) for five minutes. Supernatants were aspirated and discarded, after which the resulting latex pellets were resuspended at 0.2% (w/v) solids in the test buffer used previously.

Three aliquots (25 ul each) of each test sample were than directly pipetted onto the more porous side of glass microfiber paper. Interaction was observed by fluorescence under long wave UV light. Fluorescent spots were photographed using UV transillumination, and a Polaroid camera. FIG. 4 shows these results.

Latex samples were added to the glass microfiber paper in 50 mM sodium phosphate (pH 2, 4, 6, 8, 10 and 12) with antibody coupled to the latex (samples 2, 4, 6, 8, 10 and 12) or without antibody coupled to the latex (samples 2R, 6R, 8R, 10R and 12R). Additional samples in 50 mM acetic acid (pH 3) with antibody coupled to the latex (sample HAC-3) and without antibody coupled to the latex (HACR-3) were also evaluated.

The figure shows that when antibody is present on the latex, the interaction between latex and glass microfiber paper increases dramatically—i.e., spot diameter decreases, showing much less diffusion/dispersion on the paper, and "tighter" positioning. This permits the manufacture of test strips with the receptor carrying particles in precise, chosen positions.

The data show that the enhanced interaction varies with pH. When the pH of the test buffer is lower than antibody pI values (i.e., pH 2–4), the degree of dispersion is lessened.

EXAMPLE 3

Further studies were carried out which confirmed one of the conclusions reached from the experiments of Example 2—that the presence of a charged receptor on the particles helped in reducing dispersion.

Rabbit anti-strep A antibodies, as described supra, were correct together with the glass microfiber paper of the prior examples. Conjugates of anti-strep A antibodies and peroxidase (POD) were prepared by generally following Nakane et al., J. Hist & Cyt. 22(12):1084–1091 (1974). In addition, Group A streptococcal carbohydrate antigen was prepared, generally following Kholy et al., Appl. Microbiol. 28(5):836–839 (1974).

Devices in accordance with FIG. 2 were prepared. The antibody described supra was diluted to either 250 ug/ml or 600 ug/mL in 50 mM sodium phosphate, at pHs of 2, 4, 6, 8, 10 or 12, or in 50 mM acetic acid, at pH 3. A 12 ul quantity of antibody at both concentrations and at the various pHs was applied onto glass microfiber test regions to provide evaluation materials. Each test strip was prepared in duplicate for both concentrations, at all pHs listed. The strips were dried at 37° C. for one hour.

In the tests, a 270 ul volume of neutral pH buffer was added to each of the duplicate test strip's glass microfiber paper, while the second of the strips received 2 ng/ml Group A streptococcal carbohydrate antigen. This antigen had been prepared following Kholy et al., App. Microbiol. 28(5):836–839 (1974). Following application of either control or antigen, 35 ul volumes of 4 U/ml peroxidase labeled rabbit anti-strep A antibody conjugates were applied, and incubated for one minute. After this, 1 ml samples of sodium perborate tetrahydrate in PBS were applied to the sponges of the strips. The strips were observed visually, after 15 minutes for color reactions to indicate binding of the anti-strep A antibodies to the paper.

Figure 5A:
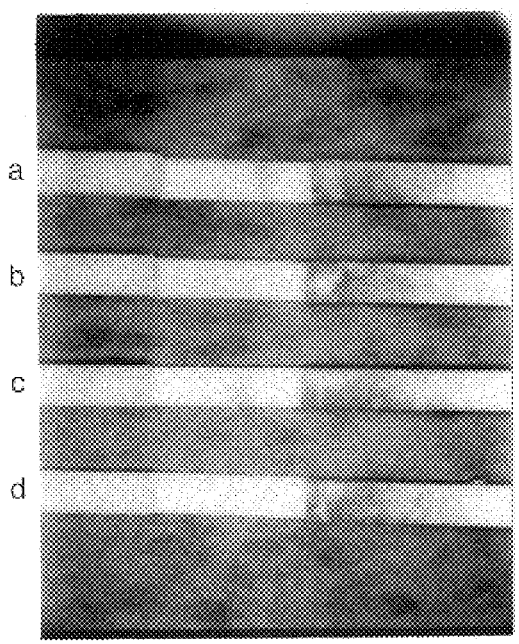
FIG. 5 depicts the pH effect with respect to interaction of test carrier and charged material.
Figure 5B:
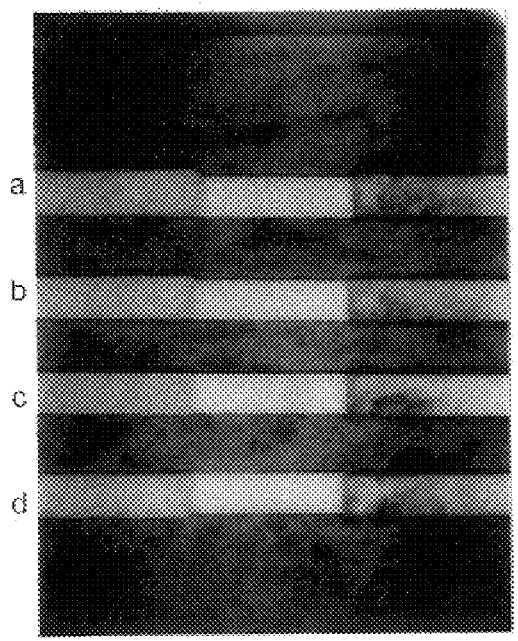

FIG. 5 shows typical results, demonstrating what is referred to as the pH effect. At pH 4, a color reaction was observed, but not at pH 10. Generally, when the pH value was below that of a typical pI value for antibodies (range of 5.6 to 7.7), color reactions were observed in both phosphate and acetate buffers. As pHs increased from 6 to 10, the color reaction gradually diminished.

No color reaction was observed in the absence of Group A streptococcal carbohydrate antigen, which suggests specificity and that the binding of antibody to glass microfiber paper in the manner described herein does not prevent interaction with antigen. Thus, strips prepared in the manner described herein can be used in qualitative immunoassay devices.

EXAMPLE 4

Mobility of underivatized fluorescent latex was compared to the mobility of latex-antibody conjugates. Devices and reagents were prepared as described supra, as was the protocol for reagent application. Test buffer for re-suspension of latex and latex-antibody conjugates was either 50 mM sodium phosphate, at pH 2 or at pH 12, or 50 mM acetic acid, at pH 3. Interaction of latex with the paper strip was observed via ultraviolet light fluorescence before and after strip development. Exemplary photographs are presented in FIG. 6.

Figure 6A:
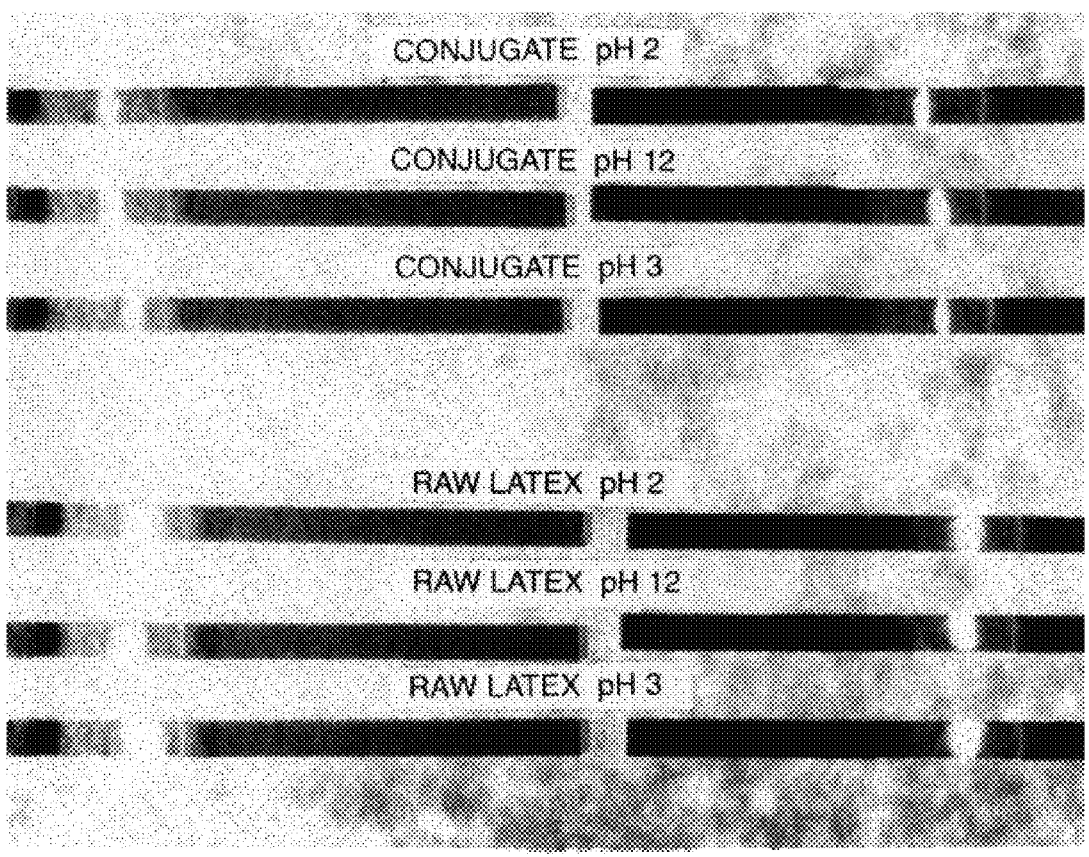
FIG. 6 compares mobility of treated and untreated particles.
Figure 6B:
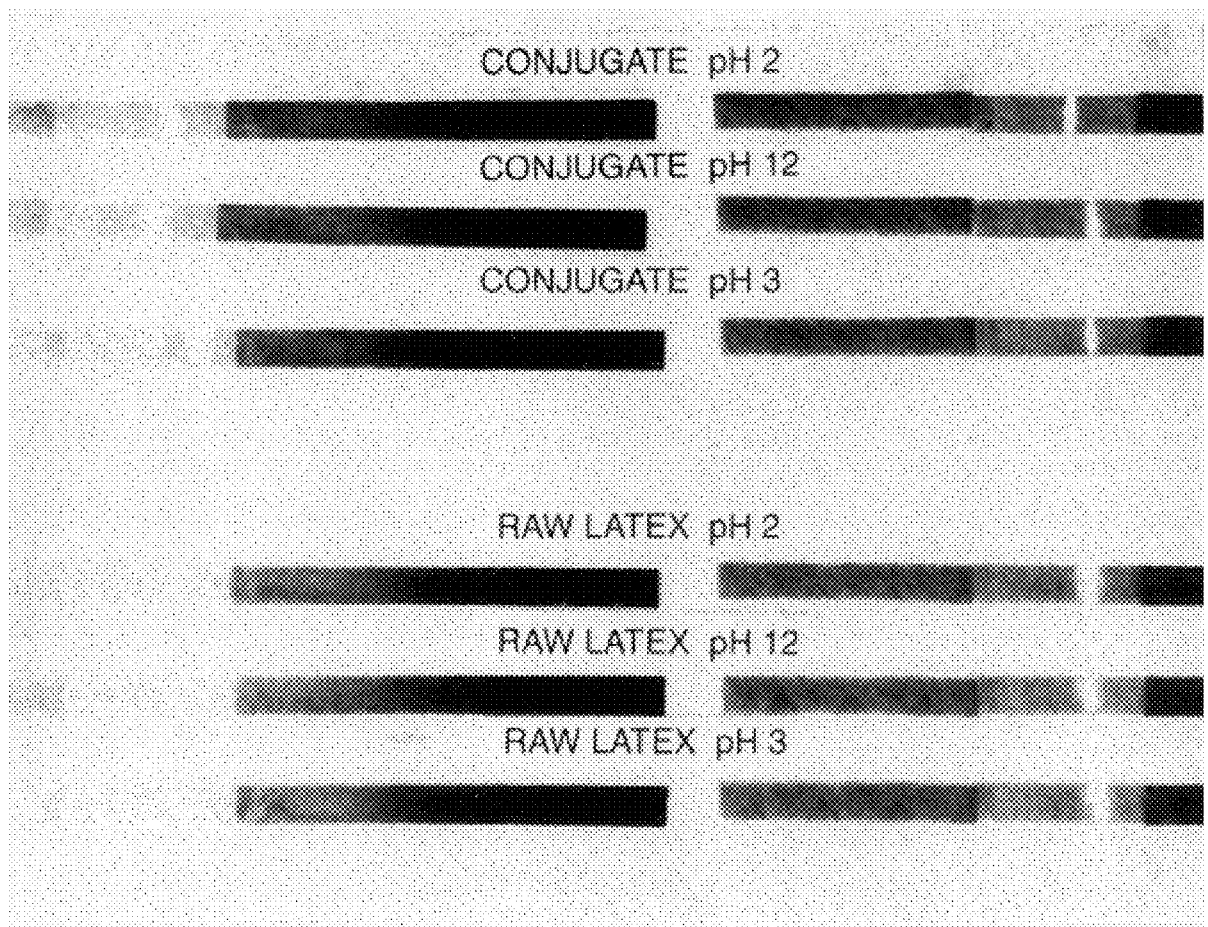

FIG. 6, it will be seen, supports the contention that when antibody is present in the latex, it plays an essential role in the interaction with the test support (e.g., glass microfiber paper). It should be noted, e.g., that there is a less distinct band for raw latex prior to strip development, and a reduction in band fluorescence for raw latex after the strip was developed.

EXAMPLE 5

The foregoing examples showed the feasibility of using antibodies in the invention described herein. Other proteins are also usable, as is now shown.

Recombinant, HIV-1 proteins containing immunodominant regions for the p24 and gp41 molecules were obtained, as was human IgG from an HIV-1 positive patient which exhibited high anti-gp41 reactivity. Mouse monoclonal anti-HIV-1 p24 antibodies were also secured, as were goat anti-human IgG and goat anti-mouse IgG peroxidase conjugates.

The p24 protein was supplied in 0.1M sodium phosphate buffer at pH 8.5, and containing 1% SDS (w/v). This was diluted from 23.9 mg/ml to 4.0 mg/ml, using 0.01M sodium phosphate buffer at pH 7.5. Buffer was exchanged against sodium phosphate buffer, using a 10 KDa Centricon Unit. Similarly, gp41 recombinant protein was exchanged from 0.1M sodium phosphate buffer at pH 7.5, where the buffer contained 0.1% (w/v) SDS and 5 mM EDTA.

Test samples of the proteins were diluted to 1 mg/ml in 50 ml sodium phosphate, at pHs of 2, 4, 6, 8, 10 or 12, or in 50 ml acetic acid, at pH 3. Application protocols were exactly as described for the anti-Strep A antibodies as discussed in Example 3.

Again, following Example 3, 270 ul volumes 1:100 (v/v) dilution of murine monoclonal anti-HIV p24 antibodies were applied to one of the duplicate strips, while equivalent volumes of HIV negative serum samples were added as controls to the other strip. This was followed by addition of 35 ul aliquots of goat anti-mouse IgG peoxidase (1:200 (v/v) dilution) and goat anti-human IgG peroxidase conjugates (0.1 U/ml) to the strips, and then 1 ml of a PBS solution containing sodium perborate tetrahydrate. Again, as in Example 3, visual color was observed, this time after 10 minutes. Formation of color indicates either the presence of p24: mouse IgG complexes, or p24: human IgG complexes.

Figure 7:
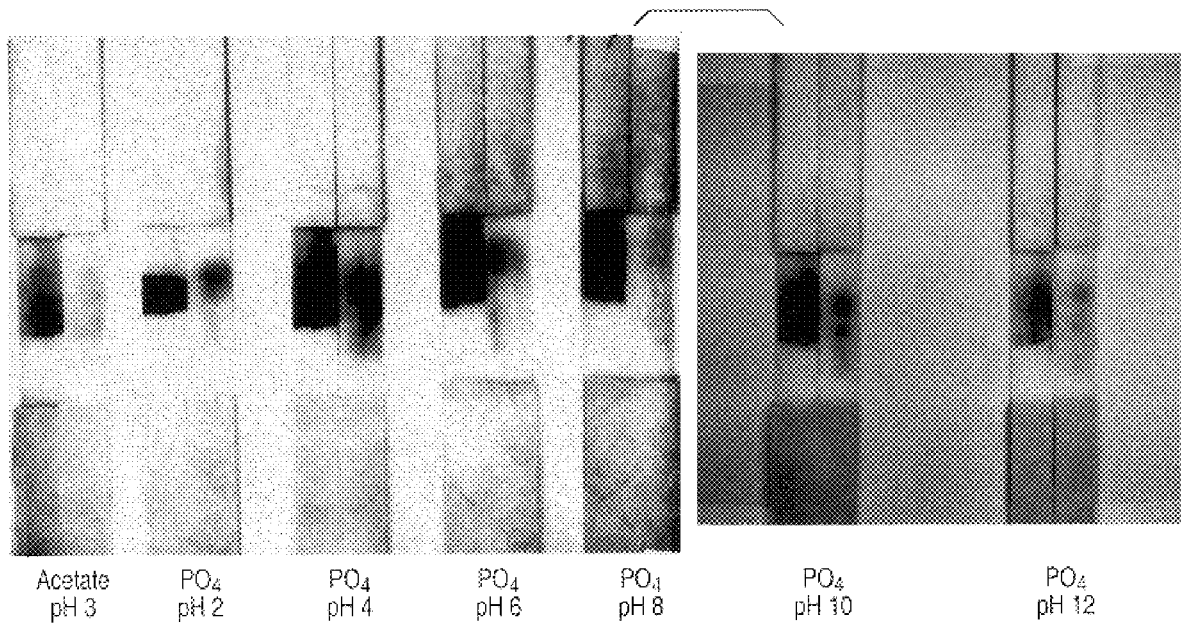
FIG. 7 presents data obtained in an HIV test strip, where p24 is receptor.

FIG. 7 shows these results. The "first" strip of each sample, which used the murine samples, showed that where protein impregnation took place at low pH (2 and 3), there was extremely tight binding to the filter paper. As pH levels increased, mobility increased. While negative samples did show some non-specific binding, all samples were far less reactive than the positive strips.

EXAMPLE 6

Figure 8:
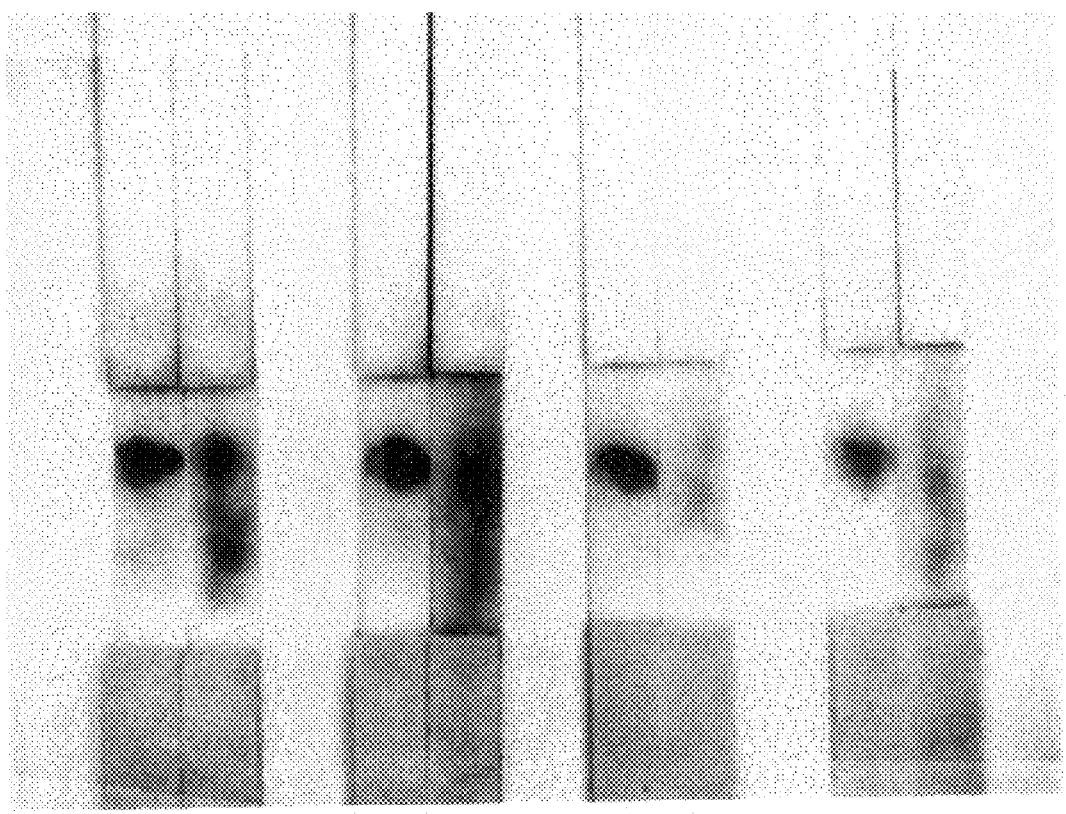
FIG. 8 parallels FIG. 7, but used gp41 as receptor

The protocol used in Example 5 was used to test gp41, the only differences being that the positive control was purified human anti-HIV gp41 IgG (62 ug/ml), and goat anti-human IgG peroxidase conjugate (0.1 U/ml) was used on both strips. The photograph of FIG. 8 shows, yet again, that there was a correlation between mobility and increased pH.

EXAMPLE 7

Strip elements as described herein and as shown in FIG. 2, were used for detection of Group A streptococci. Matrix 20 was first prepared by cutting a piece of Whatman glass fiber paper with polyvinyl alcohol fiber into a strip 2.8 cm long and 0.6 cm wide. The first portion of this strip was impregnated with 6–12 ul of a 0.1% (w/v) solids suspension of 0.4–0.5 um polystyrene latex having nonimmune rabbit IgG coupled to its surface. The middle portion of this strip was impregnated with a similar suspension of latex coupled to affinity-purified rabbit-anti-Group A Strep IgG. The end portion of the matrix was impregnated with both a conjugate of rabbit-anti-Group A Strep IgG coupled to latex and 6 ul of a solution of purified Group A Strep carbohydrate antigen, at a concentration of 60–80 ng/ml. The matrix was dried at 35° C. for approximately 20 minutes. This produced a complete matrix having a linear array of solid phase zones representing a true negative control "21", a test result zone "22" and a true positive control "23". One end of the matrix underlapped 2 mm of a 6.5 cm long and 0.6 cm wide strip of 320 paper "24", impregnated at waste "25" with approximately 60 ul of a 100 mg/ml aqueous solution of sodium azide. The opposite end of the matrix underlapped 4 mm of 1.2 cm long and 0.6 cm wide strip of X6212 Vispore. A 1.2 cm long and 0.6 cm wide strip of double stick adhesive was placed atop the Vispore. A strip of paper "27", measuring 1.5 cm long and 0.6 cm wide was positioned atop the double stick adhesive. The strip of paper had been impregnated with approximately 50 ug of a chromogenic substrate for peroxidase, i.e., 4-methoxy-1-naphthol, and dried for 15 minutes at 40° C. The paper overlapped the matrix component by 2 mm and thus established direct fluid contact with the matrix through the porous Vispore. A 1 cm long and 0.6 cm wide strip of double stick adhesive "28" was placed atop the paper 3. The adhesive was positioned in a manner which created a 0.5 cm "window" on the top surface end of the paper 27 at a position furthest from the matrix component. Finally, a sponge "26" measuring 4 cm long and 0.6 cm wide was fixed to the top of component 28. All strip components overlapped as indicated to form a continuous strip and were mounted on a 13 cm long and 0.6 cm wide piece of polyester carrier foil using hotmelt and/or double stick adhesives.

Strips constructed as described were used for the detection of Group A streptococci. Swabs, spiked with 0, $2.5 \times 10^4$, $5 \times 10^4$ and $1 \times 10^5$ Group A streptococcal colony-forming units (CFUs) were placed in small glass test tubes and subjected to a standard two minute micronitrous acid extraction following E-Kholy et al., supra to release the group specific carbohydrate antigen from the cell wall of the intact streptococci. Following extraction, the nitrous acid extract was neutralized with a weak base and 250 to 300 ul of the neutralized extract was applied in a dropwise fashion to the matrix component of the strip element between points 21 and 22. Next, 30–35 ul of a 5 unit/ml peroxidase labeled rabbit anti-strep A conjugate preparation in a buffer was applied to the same location of the matrix. In a final step, 1.2 ml of a phosphate buffered saline solution containing sodium perborate tetrahydrate was applied to component 26 of the strip element. All strips to which extracted group A streptococcal CFUs were added exhibited blue stripes at both of positions 22 and 23 of the strip matrix component. Strips run with extracts not containing group A streptococcal CFUs exhibited a blue line at position 23 only. The blue coloration on the matrix was indicative of the action of peroxidase on the chromogenic substrate 4-methoxy-1-naphthol in the presence of hydrogen peroxide at the zones depicted by 22 and 23. The irreversible inhibition of peroxidase by interaction with the sodium azide in waste zone 11 of the absorptive reservoir 24 prevented substantial color development in this reservoir. This helped to preserve the stability of the test results on the matrix component by eliminating the possibility of back diffusion of color onto the matrix during the evaporative drying of the strip element.

EXAMPLE 8

To test the flexibility of the strip device for use with alternate enzyme/substrate signal generating systems, strips were constructed and assayed in a fashion identical to that described in Example 7 with the following exceptions: component 27 was impregnated with approximately 50 ul of a solution of 5-bromo-chloro- 3-indolyl phosphate (1–2 mg/ml) ("BCIP") and nitrobluetetrazolium (0.25–0.5 mg/mL) (NBT), no signal inhibitor was incorporated into component 11, and the assay was performed using 40–50 ul of a 5–10 unit/ml alkaline phosphatase labeled rabbit anti-strep A conjugate and 50 mM 2-amino-2 methyl-1-propanol containing wash buffer. All strips to which extracted group A streptococcal CFUs were added exhibited purple bands at both zones 22 and 23 of the strip matrix component. Strips run with extracts not containing group A streptococcal CFUs exhibited a purple line at zone 23 only.

EXAMPLE 9

To demonstrate the utility of the strip device with a non enzymatic signal generating system, a gold labelled rabbit anti-Group A strep IgG conjugate was prepared with 30 nm Aurobeads™ (Janssen). The procedures and buffer systems used for preparation of the conjugate were those recommended by the manufacturer for the labeling of 30 nm particles with polyclonal antibody. An antibody concentration of 5–10 ug/ml of gold sol was used for labeling. The strip element was constructed in a fashion identical to that described in Example 7 with the exception that components 28 and 27 were not incorporated into the strip and no signal inhibitor as used in the waste zone 25 of adsorptive reservoir 24. To evaluate the strips, 250–300 ul of a neutralized nitrous acid extract containing either zero or $1 \times 10^5$ streptococcal CFUs was applied to the matrix component between zones 21 and 23. This step was followed by the application of 50 ul of a suspension of gold labeled antibody, adjusted to an absorbance at 520 nm of 5.0 to 7.0, to the same region of the matrix. In the final step of the assay, 1.2 ml of a phosphate-buffered saline wash solution was added to component 26. Strips to which neutralized extract containing group A streptococcal CFUs was added exhibited red lines in zones 22 and 23. Strips receiving extract void of Group A streptococcal CFUs exhibited a red line in zone 23 only.

EXAMPLE 10

To demonstrate the utility of the strip device with an "on board" signal generating system, strips were constructed in a fashion identical to that described in Example 1 with the exception that component 27 contained the gold labeled antibody used in Example 9 in dry form. Strips were evaluated by applying neutralized nitrous acid extracts with or without streptococcal CFRs to the matrix component as described in Example 9. Following application of sample to the matrix, 1.2 ml of phosphate buffered saline wash solution was added to component 27. The gold labeled rabbit anti-strep A IgG released from component pad 27 bound to group A antigen captured in zones 22 and 23 on strips exposed to sample containing group A streptococcal CFUs. Strips exposed to extracts void of group A streptococcal CFUs exhibited a red line at zone 23 only.

EXAMPLE 11

To demonstrate the use of the strip device in a dipstick format, strips were prepared as described in Example 1 with the exception that component 26 was not incorporated in the strip element. Sample and conjugate application was performed as described in Example 7. In the final step of the assay, strips were placed into 12×75 mm test tubes containing 500 ul of phosphate-buffered saline with a peroxide generating compound such that component 3 was brought into contact with the wash solution. Strips exposed to sample containing group A streptococci exhibited blue lines at zones 22 and 23. Strips exposed to sample void of group A streptococci exhibited a line at zone 9 only.

EXAMPLE 12

To demonstrate the use of the strip device for the detection of other analytes, strips were constructed and assayed in a fashion similar to that described in Example 7 with the following exceptions: component 20 was impregnated with 12 ul of a 0.1% (w/v) solids suspension of 0.4–0.5 µm polystyrene latex coated with p24 or gp41 (HIV-1 antigens) recombinant peptides or a 1 mg/ml solution of the individual purified proteins and no negative or positive control lines (zones 21 and 23) were included in 20. Additional differences included: (1) no signal inhibitor incorporated into the waste zone 11 of component 10, (2) human serum HIV-1 positive and negative samples (1:100 v/v) dilutions) or specific murine monoclonal antibodies (e.g., NEN mouse, anti-HIV- 1 p24) were used as controls and (3) goat-anti-human IgG and anti-mouse IgG-peroxidase conjugates were used as signal generating reagents. Serum samples containing antibody to either p24 or gp41 when utilized with this device generated a visible line (22) of the type described in Example 7 whereas no signal was generated with negative serum samples.

EXAMPLE 13

To demonstrate the use of the strip device for the detection of other analytes, strips were constructed and assayed in a fashion similar to that described in Example 7 with the following exceptions: component 20 was impregnated with 12 µl of 0.2% (w/v) solids suspension of 0.4–0.5 µm polystyrene latex coated with mouse monoclonal anti-βhCG antibody (zone 22) and a positive control (zone 23) consisting of sheep polyclonal anti-mouse IgG antibody coated on the above mentioned latex. In those preliminary experiments no negative control (zone 21) was utilized. Additional differences included: (1) no signal inhibitor was incorporated into component 24, (2) hCG samples (0, 50 and 500 mIU/ml) in both PBS and human urine were used as controls and (3) mouse monoclonal anti-holo hCG-HRP conjugate was used as the signal generating reagent. An anti-holo hCG antibody is one which binds to an epitope created by the α and β chains of hCG, and only binds to such an epitope. Differences in the assay format were volume related; that is, 150 µl of sample, 50 µl of mAb anti-holo hCG-HRP (12 U/ml) and 850 µl of run buffer.

Similar results were observed with strips having the mAb anti-holo hCG-POD conjugate dried in component 20 prior to test zones 22 and 23, which eliminated the need for manual liquid conjugate addition.

Urine samples containing hCG when utilized in this device generated two visible lines (zones 22 and 23), one being the test region the other being the positive control. Urine samples devoid of hCG exhibited a single visible line (zone 23) in the positive control region.

EXAMPLE 14

A test strip was prepared and used to analyze hCG in urine. The strip was identical to Example 15, except mAb anti-holo hCG was conjugated to alkaline phosphatase; component 27 was impregnated with BCIP/NBT (0.5 mg/ml of each in methanol) and an alkaline phosphatase run buffer was used.

Similar results were observed with strips having the mAb anti-holo hCG alkaline phosphatase conjugate dried in component 20 prior to test zones 22 and 23 which again eliminate the need for manual liquid conjugate addition.

Urine samples containing hCG when utilized in this device generated two visible lines (zones 22 and 23), one being the test region the other being the positive control. Urine samples devoid of hCG exhibited a single visible line (zone 9) in the positive control region.

The foregoing examples thus show the features of the invention. These features include, e.g., a process useful for making a test element useful in analytical processes, such as diagnosis of various parameters. This manufacturing process, in its broadest embodiment, requires applying a charge to an analyte specific receptor, and then applying this composition of matter to a test element carrying an opposite charge. The interaction of charges immobilizes the composition of matter sufficiently so that adhesives are not necessary to render the resulting device useful.

The composition of matter, as the phrase is used herein may refer to something as simple as a sample of analyte specific receptor. Some potential analyte specific receptors are discussed infra. In a preferred embodiment of this aspect of the invention, the composition of matter also contains a carrier, to which the analyte specific receptor is bound or to which it adheres. Again, examples of carriers are given infra.

In a particular preferred embodiment, the composition of matter is treated to impart a charge thereto by contacting with a solution having a pH other than the isoelectric point ("pI") of the analyte specific receptors making up or contained in the composition of matter. The manner in which this type of contact is carried out, including the determination of pI of the analyte specific receptors, is well known to the art and does not require elaboration herein.

As indicated, the composition of matter is applied to a test element which carries a charge. It is to be noted that some of the materials generally used for test elements, including papers, carry a charge. When such materials are used, no further treatment is necessary to ensure immobilization of the composition of matter to the test element. When the test element does not carry a charge, however, it can be treated to carry one which is opposite to that carried by the composition of matter. There are many standard ways of doing this, for example, by treating a cellulose containing test element with periodate, exposing a nylon test element to acidic condition or by subjecting the material to an electric field.

The nature of the analyte specific receptor may vary. Common receptors include antibodies, both polyclonal and monoclonal, as well as binding fragments of these, and oligovalent or "polymerized" antibodies. The receptors may be other proteins such as protein A or protein G, and since the receptor may also be an antigen when the assay determines antibodies (note the HIV assays, supra), any binding protein may serve as an analyte specific receptor. Similarly, receptors such as a lectin may contain carbohydrate, lipid or nucleic acid molecules, as well as the aforementioned proteins. Biotin and avidin/streptavidin as well as derivatives of these are encompassed herein, as are receptors which have been treated in a manner which does not change their ability to bind analyte. Examples of such modifications need not be given here, as the art is presumably familiar with, e.g., succinylation of proteins to render these more amendable to solid phase binding.

The analyte specific receptors are chosen, of course, on the basis of the aim of the assay. Typical tests include, e.g., assays for etiological agents for infectious diseases, including, but not limited to, the sexually transmissible diseases ("STD"). The receptor is thereby chosen to bind an epitope of the causative agent. In addition to the specific microorganisms mentioned supra, Chlamydia, Rubella, Cytomegalovirus, Toxoplasma, Neisseria, Herpes, and Human Immunodeficiency Virus are some of the organisms which can be assayed.

When carriers are used in connection with the receptors described herein, the "carrier" may be any of the materials associated with the diagnostic apparatus. These include, but are not limited to carriers of a specific shape (e.g., a bead or sphere), or of specific synthetic or natural materials, such as latex, glass, cross-linked carbohydrates, agarose, polystyrene, dextran, mica, and diatomaceous earth. These carriers may be solid or porous. Especially preferred are carriers which are of a uniform size, and are from about 1.0 nm to about 20 um in diameter. Especially preferred are 0.3 to 1.0 um particles, those of 0.4 to 0.5 um diameter being particularly preferred.

After the particles have been applied to the test carrier as indicated, the resulting material may be used to manufacture the diagnostic apparatus. Such apparatus are another aspect of the invention, including multizoned materials. The most salient feature of the apparatus of the invention includes the presence of three distinct zones, each of which comprises absorptive material. These zones are presented in a way so that a fluid or sample being analyzed may move through each of these. The first zone is characterized by containing a non-reactive immobilized material, such as non-binding IgG. These materials are useful in allowing the user to judge the integrity of the particular device being used.

The second zone is manufactured so as to comprise an analyte specific receptor, which may, but need not be, attached to the absorptive material in the manner described supra. The third zone contains both analyte receptor and analyte to be determined. This combination ensures that, if the device is functional, binding will take place in the third zone. The analyte in the third zone may, but need not be dissolvable in sample being tested. The presence of immobilized reactant ensures that the analyte contained therein will be immobilized, whether it is dissolvable or, e.g., present on carriers such as those described supra.

It is indicated, supra, that the analyte specific receptor of the apparatus of the invention may be any of the types of receptors discussed supra. Similarly, these receptors may be positioned on any of the carriers described supra. The support used to make the test carriers as well as the apparatus may be fibrous (e.g., it may contain glass fibers), bibulous (e.g., containing absorptive paper or cellulose), and may also be membranous, such as a gel, film, web, etc.

There are many different embodiments of the apparatus and processes of the invention described herein, all of which are useful to the skilled artisan. For example, one can apply basic principles of diagnostic analysis to make variants of the devices described herein. As has been pointed out, the immobilization method described leads to the positioning of an analyte specific receptor. A second receptor may also be incorporated into the test carrier or apparatus. In such a situation, the second receptor may bind with either the analyte of interest, thereby creating a sandwich structure of first receptor - analyte - second receptor, or it may bind directly to the first receptor, thereby competing with analyte for binding. In either of these embodiments, it is desirable that the second receptor carry a label which provides a detectable signal. The label chosen may be an enzyme, a gold sol, a dye sol, a colored particle, a fluorescer, a chemiluminescer, or a radiolabel. When an enzyme, such as β galactosidase, peroxidase, alkaline, phosphatase, urease, or glucose oxidase is used, the test carrier may also contain a substance which reacts with the enzyme to provide a signal, generally but not exclusively a colored one. The listed enzymes must be taken as examples of the enzymes which may be used. The roster is not comprehensive.

It is well recognized that in many situations, including, e.g., diagnosis of STDs, it is desirable to analyze a sample for more than one analyte at the same time. The invention provides a method for making devices useful for such polyanalyte analysis, wherein a plurality of different compositions of matter are used, these being positioned at different areas of a test element.

Various configurations are also available for the construction of test apparatus in accordance with the invention. The description of the multi-zoned devices of the invention provided supra explains how all three zones contain immobilized reactant. As the reactants in both the second and third zones must bind the analyte of interest, it is sometimes desirable, although not necessary, that these be identical. For example, in a thyroxin assay, one of the zones 2 and 3 may contain immobilized anti-thyroxin antibodies, and the other immobilized thyroxin binding protein. Both zones may also contain one of these. Similarly, in assaying for HIV antibodies, two different peptides may be used in the two zones, or the same peptide may be used in both. Also, as the examples show, there are antibodies which bind only to epitopes created when two single chains combine to form a dimer, and antibodies which are specific to only one chain. This type of antibody diversity may also be exploited in the invention.

The first zone, as indicated, contains an active immobilized reactant. The choice of material used herein may vary, although it is preferred to use an inactive form of the immobilized reactant in one or both of the second and third zones. Inactivation may be secured by treating with heat or various chemical agents, e.g.

In constructing the apparatus of the invention, it may be desirable to configure the zones such that the flow of a sample is controlled. This can be accomplished, e.g., by having two contiguous zones positioned so that the direction of fluid flow in one is perpendicular to flow in the other.

While the devices disclosed herein require three zones, they are not limited to only three. Indeed, it may be preferred to add a fourth zone, positioned downstream of the third zone. The practical advantages of the fourth zone include the ability to absorb excess liquid in the device. Also, the fourth zone, as it is positioned away from the sites of immobilizing reactions, may contain various materials that allow the user to determine whether the particular test strip is still functional, as well as how far the reaction is proceeding. Among the materials which can be incorporated into the fourth zone are substances which change color in the presence of a liquid, pH indicators which change color when subjected to pH stresses, and, in a particularly useful embodiment, signal inhibitors. This embodiment is useful because frequently, excess labeled reactant or colored products of a reaction will flow into the fourth zone, and then "backwash" into one or more reaction zones. The use of an inhibitor helps to prevent this type of situation from happening.

A fifth zone may also be used, either together with the fourth zone as described, or with only the first through third zones. This fifth zone is positioned upstream of the first zone, and will contain reaction chemistry, such as a labeled receptor which takes part in the analyte reaction. This labeled receptor is released and flows into the various zones and reacts in the manner described supra. An adsorptive means will be used in connection with the fifth zone, and is in fluid contact with it, as is the fifth zone with the first zone.

Due to the contact of first and fifth zones, it may be desirable to inhibit or to regulate the flow of fluid, and in such a case an inhibition means may be incorporated, so as to direct liquid into the fifth zone and away from said first zone. The fluid then moves from the fifth zone into said first zone, but not directly into the first zone. The regulating means described herein is preferably one which directs fluid to move a vertical direction. Preferably, when all of the zones desired are configured in the manner desired, they are placed on an inert support of the type generally used in diagnostic test strips. In particular, it is preferred that the first, second and third zones be placed on an inert support.

It has been mentioned, supra, that it is possible to incorporate a second receptor into the apparatus of this invention. Incorporation into the device per se is not necessary, however, as the second receptor may be provided in a separate portion external to the actual apparatus, but as part of a kit. Such a kit may also include a separate portion of a run buffer, i.e., a material added directly to the device which is generally inert and which helps with the migration of various components of the assay through the device.

Other embodiments of the invention will be clear to the skilled artisan and need not be set forth here.

It will be understood that the specification and examples are illustrative but not limitative of the present invention and that other embodiments within the spirit and scope of the invention will suggest themselves to those skilled in the art.

We claim:

1. Process for preparing a test element useful in analysis of a sample comprising:
    (i) contacting a composition of matter which comprises an analyte specific receptor bound to a carrier with a solution which has a pH which is different from the isoelectric point of said analyte specific receptor so as to impart a charge thereto, and
    (ii) applying said charged composition of matter to an area of a test element which carries a charge opposite that of said charged composition of matter so as to bind said charged composition of matter thereon.

2. Process of claim 1, further comprising treating said test element to impart a change thereto opposite to said charged composition of matter.

3. Process of claim 2, comprising treating said test element by oxidation with periodate.

4. Process of claim 2, comprising treating said test element by placing it in an electric field.

5. Process of claim 1, wherein said analyte specific receptor comprises a protein containing molecule.

6. Process of claim 5, wherein said protein containing molecule is succinylated.

7. Process of claim 1, wherein said analyte specific receptor comprises a carbohydrate containing molecule.

8. Process of claim 1, wherein said analyte specific receptor comprises a lipid containing molecule.

9. Process of claim 1, wherein said analyte specific receptor comprises an antibody or bindable fragment thereof.

10. Process of claim 1, wherein said analyte specific receptor comprises a lectin, streptavidin, avidin, protein A or protein G.

11. Process of claim 1, wherein said carrier is porous.

12. Process of claim 1, wherein said carrier is solid.

13. Process of claim 1, wherein said carrier is a bead or sphere.

14. Process of claim 1, wherein said carrier comprises synthetic material.

15. Process of claim 1, wherein said carrier comprises a natural material.

16. Process of claim 1, wherein said carrier comprises latex, glass, a cross-linked carbohydrate, agarose, polystyrene, dextran, mica or diatomaceous earth.

17. Process of claim 1, wherein said carrier comprises particles of uniform size.

18. Process of claim 17, wherein said particles are from 1.0 nm to 20 $\mu$m in diameter.

19. Process of claim 18, wherein said particles are from 0.3 to 1.0 $\mu$m in diameter.

20. Process of claim 19, wherein said particles are from 0.4 to 0.5 $\mu$m in diameter.

21. Process of claim 1, wherein said area of said test element comprises fibrous material.

22. Process of claim 21, wherein said fibrous material comprises glass fibers.

23. Process of claim 1, wherein said area of said test element comprises bibulous material.

24. Process of claim 23, wherein said bibulous material comprises cellulose.

25. Process of claim 1, wherein said area of said test element is a membrane.

26. Process of claim 1, further comprising incorporating a second receptor into said test element, wherein said second receptor specifically binds to said analyte or to said first receptor.

27. Process of claim 1, further comprising treating a plurality of compositions of matter, each of which contains a different analyte specific receptor so as to impart a charge to each, and applying each of said compositions of matter to an area of said test element.

28. Process of claim 27, wherein each of said compositions of matter is applied to a separate area of said test element.

* * * * *